United States Patent [19]
Noda et al.

[11] Patent Number: 5,389,380
[45] Date of Patent: Feb. 14, 1995

[54] SUSTAINED RELEASE PHARMACEUTICAL PREPARATION AND PROCESS FOR PREPARING THE SAME

[75] Inventors: Kazuo Noda, Takarazuka; Masao Kobayashi, Kyoto; Takashi Osawa; Toru Maejima, both of Toyonaka, all of Japan

[73] Assignee: Tanabe Seiyaku Co., Ltd., Osaka, Japan

[21] Appl. No.: 120,859

[22] Filed: Aug. 31, 1993

Related U.S. Application Data

[63] Continuation of Ser. No. 863,170, Apr. 3, 1992, abandoned.

[30] Foreign Application Priority Data

Apr. 8, 1991 [JP] Japan ................... 3-075335

[51] Int. Cl.$^6$ .............................................. A61K 9/16
[52] U.S. Cl. .................... 424/490; 424/489; 424/498
[58] Field of Search ............. 424/490, 489, 488, 472, 424/495

[56] References Cited

U.S. PATENT DOCUMENTS

| | | | |
|---|---|---|---|
| 4,443,428 | 4/1984 | Oshlack | 424/488 |
| 4,684,516 | 8/1987 | Bhutani | 424/19 |
| 4,720,387 | 1/1988 | Sakamoto | 424/472 |
| 4,834,985 | 5/1989 | Elger | 424/490 |
| 5,068,112 | 11/1991 | Samejima | 424/495 |

FOREIGN PATENT DOCUMENTS

| | | |
|---|---|---|
| 0222411 | 11/1986 | European Pat. Off. . |
| 0253684 | 7/1987 | European Pat. Off. . |
| 0293070 | 3/1988 | European Pat. Off. . |
| 57-171918 | 10/1982 | Japan . |
| 60-072814 | 4/1985 | Japan . |
| 64-002554 | 1/1988 | Japan . |

OTHER PUBLICATIONS

Chem. Abstr., vol. 105, 1986, pp. 383, 105:178467g "Coatings for Sustained . . . " Sasagawa, et al.

Primary Examiner—Thurman K. Page
Assistant Examiner—William E. Benston, Jr.
Attorney, Agent, or Firm—Birch, Stewart, Kolasch & Birch

[57] ABSTRACT

A sustained release pharmaceutical preparation comprising a carrier, an effective ingredient layer containing a medicinal compound and a heat-meltable material as a binder which is formed around said carrier and a coating layer containing a non-heat-meltable dissolution-controlling agent and a heat-meltable material as a binder which is formed around said effective ingredient layer and the process for preparing the same. According to the present invention, the formation of the effective ingredient layer and the formation of the coating layer can be successively carried out in the same apparatus without using any solvents or drying step in short hours to give a sustained release pharmaceutical preparation which can release a medicinal compound at a suitable dissolution rate according to the physical property of the medicinal compound.

5 Claims, 4 Drawing Sheets

□——□ Core
×——× Pharmaceutical preparation 1
◇——◇ Pharmaceutical preparation 2

□——□ Core

×——× Pharmaceutical preparation 3

◇——◇ Pharmaceutical preparation 4

△——△ Pharmaceutical preparation 5

SUSTAINED RELEASE PHARMACEUTICAL PREPARATION AND PROCESS FOR PREPARING THE SAME

This application is a continuation of application Ser. No. 07/863,170, filed on Apr. 3, 1992, now abandoned.

BACKGROUND OF THE INVENTION

The present invention relates to a sustained release pharmaceutical preparation and a process for preparing the same, and more particularly to a sustained release pharmaceutical preparation which releases a medicinal compound at a dissolution rate suitable for the medicinal compound and a process for easily and efficiently preparing the same.

Hitherto, a pharmaceutical preparation wherein a core containing a medicinal compound is coated around its surface with a hydrophobic material such as fat and oil or wax, has been known as a sustained release pharmaceutical preparation which releases a medicinal compound gradually.

Such sustained release pharmaceutical preparation comprises a core containing a medicinal compound as an effective ingredient and a coating layer containing a hydrophobic material around the core for controlling the dissolution of the medicinal compound.

The above-mentioned core and coating layer are usually prepared by separate processes respectively. That is, the core containing a medicinal compound is prepared by the usual process such as wet granulation or dry granulation and then the coating layer is provided thereon by another process with another equipment.

Various techniques have been reported with respect to processes for preparing the coating layer which controlls dissolution rate of an effective ingredient. As processes for preparing the coating layer containing a hydrophobic material, the following processes have been known.

As a general process, a hydrophobic solid material is dissolved in an organic solvent and then the obtained solution is sprayed on the surface of a core containing a medicinal compound followed by drying to coat the solid particle with the hydrophobic solid material. In such method, however, a halogenated hydrocarbon such as carbon tetrachloride or chloroform, a hydrocarbon such as hexane or benzene, a lower alcohol such as methanol or propanol, a ketone such as acetone and the like which are harmful to human body, are usually used as an organic solvent. Therefore, considerable equipments are required to secure the safety of workmen and to prevent air pollution as to the preparation of sustained release pharmaceutical preparations. Furthermore, considerable equipments and time are also required to remove the above-mentioned solvents from coated pharmaceutical preparations. Nevertheless there still remain the organic solvents in the pharmaceutical preparations.

In order to solve the above-mentioned problems, there is proposed a powder coating process wherein fine particles of a hydrophobic solid material are spread on the surface of a core containing a medicinal compound while rolling the core with spraying an aqueous solution of a binder such as methylcellulose which is a polymer compound soluble in water or an alcohol, thereby the hydrophobic solid material adhering to the core, in Japanese Unexamined Patent Publications No. 99009/1988 and No. 27424/1988. In this method, the amount of an organic solvent to be used is considerably reduced in comparison with that in the method wherein a hydrophobic material is coated by spraying an organic solvent solution thereof, or such organic solvents are not required. However, there still remain problems concerning equipments and time required in drying step and concerning the safety on using organic solvents, because water or organic solvents are still used.

As a process for coating a hydrophobic material such as fat and oil or wax without using water nor any organic solvent, there is a fused coating process. As one of a fused coating process, there is known a process wherein a heat-meltable material is molten with heating and then sprayed for coating. However, this process requires a melting pot and pipes, nozzles and the like which can be kept high temperature as equipments for coating the molten heat-meltable material. In addition, the workability is low in this process.

On the other hand, there is known a process wherein powder of a heat-meltable material is spread on powder or tablets and the mixture is rolled with heating to coat the powder or tablets with the heat-meltable material in Japanese Examined Patent Publication No. 3789/1965, as a process for coating powder or tablets with a heat-meltable material on their surface. According to this process, the coating can be carried out without using organic solvent at all nor requiring particular pipe arrangement. As a process for forming a dissolution-controlling coating layer which utilizes the above-mentioned process, there discloses a process wherein a core containing theophylline as a medicinal compound and a heat-meltable material such as wax are rolled with heating and after the heat-meltable material is molten, hydrophobic fine powder such as calcium stearate is spread, thereby the hydrophobic fine powder adhering to the core in Japanese Unexamined Patent Publication No. 171918/1982. In this process, a heat-meltable material and fine powder of a hydrophobic material are added separately without mixing. Therefore, operations are complicated and there remains a problem in uniformity of the dissolution-controlling coating layer.

On the other hand, as processes which further simplify the preparation of a sustained release pharmaceutical preparation, there disclose processes wherein two steps, namely a step of preparing a core containing a medicinal compound as an effective ingredient using a heat-meltable bead and a step of forming a coating layer thereon for controlling the dissolution of the medicinal compound, are carried out successively in Japanese Unexamined Patent Publications No. 214333/1983 and No. 181214/1987. In these processes, while the surface of the heat-meltable bead is molten in fluidized-bed granulator with heating, a medicinal compound is added to the above-mentioned heat-meltable bead which serves as a carrier, thereby the medicinal compound adhering to the carrier to give core containing an effective ingredient. Successively thereto is added a water-insoluble material such as talc while fluidizing the core with heating, thereby the water-insoluble material adhering thereto to form a coating layer for controlling the dissolution of the medicinal compound. However, in these processes, the total amount of the medicinal compound and a water-insoluble material which adheres to the heat-meltable bead is limited because they successively adhere to the molten surface of the heat-meltable bead. That is, it is difficult to freely increase the amounts of a medicinal compound and a water-insoluble material and therefore it is understood that the above-mentioned processes are not suitable for controlling the dissolution rate of the medicinal compound of a sustained release pharmaceutical preparation by increasing or decreasing the coating amount of the water-insoluble material. Furthermore, in the above-mentioned processes, strict control of the temperature is required during the process, because powder adheres to a heat-meltable bead while the heat-meltable bead gradually melts from its surface.

An object of the invention is to provide a sustained release pharmaceutical preparation whose release of a medicinal compound is accurately controlled suitably for the medicinal compound, and a simple process for safely preparing the sustained release pharmaceutical preparation which does not require organic solvents, by solving the above-mentioned problems in processes wherein organic solvents are not used and in processes wherein a core containing an effective ingredient and a coating layer for controlling the release of the effective ingredient are prepared successively.

SUMMARY OF THE INVENTION

It has now been found that the formation of an effective ingredient layer containing a medicinal compound and the formation of a coating layer for controlling the dissolution of the medicinal compound can be successively carried out with ease and high accuracy without using any solvents such as water or organic solvents by a process wherein a rapid release core is prepared by spreading a mixture containing a medicinal compound, a heat-meltable material as a binder and, if necessary, one or more non-heat-meltable material to a carrier at a temperature at which the heat-meltable material can melt, thereby the mixture adhering around the carrier, and then a coating layer for controlling the dissolution of the medicinal compound is formed by spreading a mixture containing a water-insoluble and non-heat-meltable dissolution-controlling agent and a heat-meltable material as a binder under the same condition in the preparation of the core, thereby the mixture adhering around the core.

That is, there is provided a sustained release pharmaceutical preparation comprising
(1) a carrier,
(2) an effective ingredient layer which is formed around the carrier, said effective ingredient layer containing a medicinal compound and a heat-meltable material as a binder, and
(3) a coating layer which is formed around the effective ingredient layer, said coating layer containing a non-heat-meltable dissolution-controlling agent and a heat-meltable material as a binder.

Furthermore, there is provided a process for preparing a sustained release pharmaceutical preparation which comprises:
(1) adding a mixture containing a medicinal compound and a heat-meltable material to a particulate carrier with rolling the carrier at a temperature at which the heat-meltable material can melt, to form an effective ingredient layer containing the medicinal compound and the heat-meltable material as a binder around the carrier, thereby providing a core, and
(2) successively adding a mixture containing a heat-meltable material and a non-heat-meltable dissolution-controlling agent to the core under the same condition as in the step (1) to form a coating layer containing the non-heat-meltable dissolution-controlling agent and the heat-meltable material as a binder around the core.

DETAILED DESCRIPTION

Figure 1:
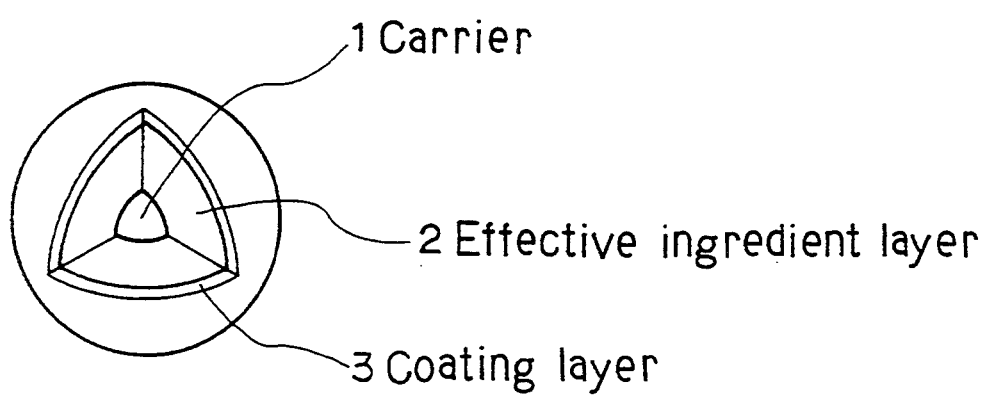
FIG. 1 is an elevation partly in section showing the structure of a sustained release pharmaceutical preparation of the present invention.

A sustained release pharmaceutical preparation of the present invention is, as shown in FIG. 1, for example, a granule comprising a carrier 1, an effective ingredient layer 2 containing a medicinal compound and a heat-meltable material as a binder which is formed around the carrier 1 and a coating layer 3 containing a water-insoluble and non-heat-meltable dissolution-controlling agent and a heat-meltable material as a binder which is formed around the effective ingredient layer 2.

A medicinal compound which can be contained in the sustained release pharmaceutical preparation of the present invention is not particularly limited. As such medicinal compound, there are, for example, calcium antagonists such as diltiazem hydrochloride, verapamil hydrochloride, nicardipine, nitrendipine and nimodipine, antiasthmatic agents such as theophylline and trimetoquinol, water soluble vitamins, antibiotics, antimalignanttumor agents, antipyretic analgesics, antihyperglycemic agents and the like.

As a heat-meltable material to be used in the effective ingredient layer of the sustained release pharmaceutical preparation of the present invention, a substance which is in a powdery state at an ordinary temperature and melts at a temperature of from 30° to 100° C. can be used. For example, a higher fatty acid, a higher aliphatic alcohol, an ester of a higher fatty acid, an ester of a hydroxyl group-containing higher fatty acid, a polyethyleneglycol and the like can be used. On the other hand, as a heat-meltable material to be used in the coating layer, the above-mentioned substances which are usable in the effective ingredient layer can be used except for a polyethyleneglycol. The heat-meltable material usable in the coating layer can be used, if desired, together with a polyethyleneglycol.

Higher fatty acids include, for example, a saturated or unsaturated fatty acid having 10–32 carbon atoms and the like. Higher fatty aliphatic alcohols include, for example, an aliphatic monaromic alochol having 12–30 carbon atoms and the like. Esters of higher fatty acids include, for example, an ester of a saturated or unsaturated fatty acid having 14–24 carbon atoms and an aliphatic monaromic alcohol having 12–24 carbon atoms, an ester of a saturated or unsaturated fatty acid having 12–18 carbon atoms and glyceline, a hydrogenated compound thereof, mixture thereof and the like. Esters of a hydroxyl group-containing higher fatty acid include an ester of a hydroxyl group-containing fatty acid having 12–22 carbon atoms and an alipahtic monaromic alcohol having 12–22 carbon atoms, an ester of a hydroxyl group-containing saturated fatty acid having 12–22 carbon atoms and glyceline, an ester of a hydroxyl group-containing unsaturated fatty acid having 12–22 carbon atoms and glyceline, a hydrogenated comound thereof, mixture thereof and the like.

As concrete examples of higher fatty acids, there are, for example, capric acid, undecylic acid, lauric acid, tridecylic acid, myristic acid, pentadecylic acid, palmitic acid, heptadecylic acid, stearic acid, nonadecanoic acid, arachic acid, behenic acid, lignoceric acid, cerotic acid, heptacosanoic acid, montanic acid, melissic acid, lacceric acid, elaidic acid, brassidic acid and the like. Among these examples, myristic acid, palmitic acid, stearic acid, nonadecanoic acid and behenic acid, in particular, palmitic acid, stearic acid and behenic acid are preferable.

As concrete examples of higher alipahtic alcohols, there are, for example, lauryl alcohol, tridecyl alcohol, myristyl alcohol, pentadecyl alcohol, cetyl alcohol, heptadecyl alcohol, stearyl alcohol, nonadecyl alcohol, eicosyl alcohol, ceryl alcohol, melissyl alcohol and the like. Among these examples, cetyl alcohol, stearyl alcohol and eicosyl alcohol, in particular, cetyl alcohol and stearyl alcohol are preferable.

As concrete examples of esters of a higher fatty acid, there are, for example, an ester of a fatty acid such as myristyl palmitate, stearyl stearate, myristyl myristate, ceryl lignocerate, lacceryl cerotate or lacceryl lacecrate, natural wax obtained from animals such as lanolin, beeswax, spermaceti and shellac wax, natural wax obtained from plants such as carnauba wax and candelilla wax, glyceryl monolaurate, glyceryl monomyristate, glyceryl monostearate, glyceryl dilaurate, glyceryl dimyristate, glyceryl distearate, glyceryl trilaurate, glyceryl trimyristate, glyceryl tristearate, beef tallow, lard, hydrogenated beef tallow, hydrogenated rape seed oil, hydrogenated castor oil, hydrogenated coconut oil, hydrogenated soybean oil and the like. Although natural wax, beef tallow, lard and various hydrogenated oil contain various kinds of components, all of them can be suitably used in the sustained release pharmaceutical preparation of the present invention. For example, although shellac wax contains ceryl lignocerate as a main ingredient and ceryl cerotate, lacceryl laccerate, a free alcohol, a hydrocarbon and a resin as the other components, such shellac wax can be suitably used.

As concrete examples of esters of a hydroxyl group-containing higher fatty acid, there are, for example, triglyceryl hydroxysterate and the like.

As concrete examples of polyethyleneglycols, there are, for example, polyethyleneglycol 600, polyethyleneglycol 1000, polyethyleneglycol 1500, polyethyleneglycol 1540, polyethyleneglycol 4000, polyethyleneglycol 6000 and the like.

These heat-meltable materials can be used alone or as a suitable mixture of at least two kinds.

If necessary, the effective ingredient layer may contain non-heat-meltable pharmaceutical additives which do not melt at a temperature of at most 100 ° C. For example, generally usable pharmaceutical additives such as excipient, disintegrator, binder, coating agent, lubricant and solubilizer polymer compound and the like can be used.

As concrete pharmaceutical additives, there are, for example, excipients such as lactose, sucrose, mannitol, D-sorbitol, glucose, dextrin, calcium phosphate, magnesium silicate, colloidal silicon dioxide, aluminium silicate, calcium carbonate, calcium lactate, aluminium metasilicate, dibasic calcium phosphate, magnesium aluminometasilicate, aluminium hydroxide, magnesium hydroxide, precipitated calcium carbonate and calcium hydrogencarbonate, disintegrators such as corn starch, microcrystalline cellulose, sodium carboxymethylcellulose, calcium carboxymethylcellulose, carboxymethylcellulose, low-substituted hydroxypropyl-cellulose and sodium carboxymethylstarch, binders such as hydroxypropylcellulose, hydroxypropylmethylcellulose, methylcellulose, ethylcellulose, dextrin, sodium alginate, gelatin and hydroxypropylstarch, coating agents such as acrylic resin, pullulan, hydroxypropylmethylcellulose, hydroxypropylmethylcellulose phthalete, hydroxypropyl-methylcellulose acetate phthalete, carboxymethylethyl-cellulose, cellulose acetate, cellulose acetate phthalete, shellac and zein, polymer compounds such as chitin and chitosan, lubricants such as magnesium stearate, calcium stearate, talc, titanium dioxide, colloidal silicon dioxide, magnesium silicate, dried aluminium hydroxide gel and dibasic calcium phosphate, solubilizers such as citric acid, succinic acid, fumaric acid, malic acid, tartaric acid, maleic acid, glutaric acid, sodium bicarbonate and sodium carbonate and the like.

The particle diameters of these non-heat-meltable materials are generally at most 500 μm, preferably in a range of from 1 to 300 μm.

As a non-heat-meltable dissolution-controlling agent in the coating layer of the sustained release pharmaceutical preparation of the present invention, water-insoluble materials such as magnesium stearate, calcium stearate, talc, titanium dioxide, colloidal silicon dioxide, magnesium silicate, dried aluminium hydroxide gel, precipitated calcium carbonate and calcium sulfate which do not melt at the temperature of at most 100° C., can be used. These dissolution-controlling agents can be used alone or as a mixture of at least two kinds.

These non-heat-meltable dissolution-controlling agents are generally used as powder and the particle diameters of them are generally at most 500 μm, preferably in a range of from 1 to 300 μm.

To the coating layer, if necessary, a water-soluble and non-heat-meltable material such as lactose and marmitol can be added in order to increase the dissolution rate of a medicinal compound. A water-soluble and heat-meltable material such as polyethyleneglycol can be also added to the coating layer in order to increase the dissolution rate.

As a carrier usable in the present invention, any materials which are pharmacologically inactive and do not interact with the used medicinal compound can be used as well as commercially available granulated sucrose such as Nonpareil (trade name, Freund Industrial Co. Ltd., Japan). For example, there can be exemplified sugars or sugar-alcohols such as sucrose, lactose, mannitol and xylitol, various kinds of cellulose, various kinds of starch. Though these materials can be used as crystal thereof or as granule or beads obtained by granulating themselves alone or the mixture thereof, more spherical carriers are more suitable for coating the effective ingredient layer or the coating layer.

The particle diameters of these carriers are suitably from 10 to 2000 μm, preferably from 50 to 1500 μm, although they are suitably selected according to the size of a desired pharmaceutical preparation.

The process of the present invention can be carried out using a granulating and coating apparatus such as tumbling granulator or centrifugal fluidizing type granulating and coating apparatus which are generally used when carrying out granulation or coating. The process of the present invention can be carried out by spreading a mixture containing a medicinal compound, a heat-meltable material, and if desired, a non-heat-meltable material which are generally used as pharmaceutical additives such as excipient and solubilizer to a carrier with rolling the carrier under heating to form an effective ingredient layer containing the medicinal compound and the heat-meltable material as a binder around the carrier, thereby providing a core, and successively spreading a mixture containing a heat-meltable material and a non-heat-meltable dissolution-controlling agent to the core with rolling the core under heating to form a coating layer containing the dissolution-controlling agent and the heat-meltable material as a binder for controlling the dissolution of the medicinal compound around the core.

For example, one of the suitable process is described in the followings.

First, the forming of an effective ingredient layer on a carrier is carried out as follows. A carrier is previously put into the above-mentioned granulating and coating apparatus and rolled in it with heating at a temperature of from at least 5° C. higher than the melting point of a heat-meltable material to be used in the effective ingredient layer to 100° C. The heating temperature may be a temperature at which the heat-temperature meltable material entirely melts and therefore the temperature is not recruited to be strictly controlled. Then a mixture of the heat-meltable material, a medicinal compound and, if necessary, a non-heat-meltable pharmaceutical additive is spread with rolling the carrier, thereby the mixture adhering to the carrier. Although the mixing ratio of the heat-meltable material to the other components somewhat varies according to the combination of them, 5:95 to 50:50, preferably 10:90 to 40:60 by weight is suitable. In case that the ratio of the heat-meltable material is higher than the above-mentioned ratio, granule easily agglomerates and adheres to walls of the apparatus resulting lowerings of recovery percentage and of good product percentage. On the other hand, in case that the ratio of the heat-meltable material is lower than the above-mentioned ratio, dusting of the non-heat-meltable material increases resulting in a lowering of recovery percentage.

The rotating speed is carried out at from 50 to 500 rpm, preferably from 60 to 400 rpm, for from 3 to 300 minutes, preferably for from 5 to 180 minutes.

The thickness of the effective ingredient layer of thus obtained core is usually from 5 to 500 μm. The surface of the above-mentioned effective ingredient layer is smooth and the obtained core has high sphericity. Therefore, thus obtained core can be suitably coated with the coating layer in the second step.

Second, the forming of a coating layer on the above-mentioned core is carried out as follows. The core is rolled in the granulating and coating apparatus with heating at a temperature of from at least 5° C. higher than the melting point of a heat-meltable material to be used in the coating layer to 100° C. as in the coating step of the effective ingredient layer. The heating temperature may be a temperature at which the heat-meltable material entirely melts and therefore the temperature is not required to be strictly controlled. Then a mixture of the heat-meltable material and a water-insoluble and non-heat-meltable dissolution-controlling agent is spread with rolling the core, thereby the mixture adhering to the core. Although the mixing ratio of the heat-meltable material to the non-heat-meltable material somewhat varies according to the combination of these two components, 5:95 to 50:50, preferably 10:90 to 40:60 by weight is suitable. In case that the ratio of the heat-meltable material is higher than the above-mentioned ratio, granule easily agglomerates and adheres to walls of the apparatus, resulting lowerings of recovery percentage and of good product percentage. On the other hand, in case that the ratio of the heat-meltable material is lower than the above-mentioned ratio, dusting of the non-heat-meltable material increases resulting in a lowering of recovery percentage.

The rotating speed is carried out at from 50 to 500 rpm, preferably from 60 to 400 rpm, for from 3 to 300 minutes, preferably for from 5 to 180 minutes.

The thickness of the coating layer of thus obtained sustained release granule is usually from 5 to 100 μm. The particle diameters of the heat-meltable material to be used in the process of the present invention are suitably in a range of from 1 to 500 μm, preferable from 5 to 300 μm. The coating layer prepared according to the process of the present invention has high density and is uniform in distribution of the dissolution-controlling agent in the coating layer. Therefore high dissolution-controlling ability can be given for a sustained release pharmaceutical preparation. Furthermore, thus obtained sustained release pharmaceutical preparation has smooth surface and high sphericity, and therefore the fluidity is high.

When a medicinal compound having low solubility is used in the process of the present invention, a water-soluble and non-heat-meltable material or a water-soluble and heat-meltable material can be added to the components of the coating layer for controlling the dissolution of the medicinal compound in order to increase the dissolution rate. Such water-soluble material is generally used in a range of from 2 to 50% by weight based on the weight of the coating layer.

In the above-mentioned two steps (i.e. the formation of an effective ingredient layer on a carrier and the formation of a coating layer on the core), it is preferred to use the medicinal compound, the pharmaceutical additive and the dissolution-controlling agent in the form of powder.

According to the method of the present invention, a sustained release pharmaceutical preparation can be readily obtained without using any solvent. Further, the method of the present invention is advantageous in that the formation of core containing a medicinal compound and the formation of a coating layer can be successively carried out in the same apparatus; that there is hardly any coagulation of granule during the above-mentioned two steps; and that the dissolution rate of the medicinal compound can be readily controlled by selecting the coating amount and the coating composition.

Thus obtained sustained release pharmaceutical preparation of the present invention may be used as it is, for example, as granule, fine granule or the like. Alternatively the sustained release pharmaceutical preparation may be tabletted optionally together with an excipient, a lubricant, a disintegrator and the like to give sustained release tablets or may be filled in capsules, if necessary, together with a lubricant to give sustained release capsules.

The present invention is more specifically described and explained by means of the following Test Examples and Examples in which all percents and parts are by weight unless otherwise noted. It is to be understood that the present invention is not limited to the Examples, and various changes and modifications may be made in the invention without departing from the spirit and scope thereof.

EXAMPLE 1

Nonpareil (granulated sucrose, from Freund Industrial Co. Ltd., Japan) having the diameter of 710 to 840 μm (250 g) was put into the centrifugal fluidizing type granulating and coating apparatus (CF-360, made by Freund Industrial Co. Ltd., Japan) and rolled in it at 200 rpm at 90° C. With rolling the Nonpareil, thereto was gradually spread a mixture of diltiazem hydrochloride having the diameter of 5 to 50 μm (188 g) and hydogenated castor oil having the mean particle diameter of 25 μm (62 g), thereby the mixture adhering to the Nonpareil. Thus a core was prepared. No dusting of powder nor agglomeration of carrier and/or core was observed during the preparation of the core. Then the obtained core (200 g) was put into the above-mentioned centrifugal fluidizing type granulating and coating apparatus and rolled in it at 200 rpm at 90° C. With rolling the core, thereto was gradually spread a mixture (40 g) of hydrogenated castor oil having the mean particle diameter of 25 μm and talc having the mean particle diameter of 10 μm in the ratio of 2:8, thereby the mixture adhering to the core. Thus a sustained release pharmaceutical preparation wherein the ratio of the amount of the coating layer was 20% to that of the core was obtained (Pharmaceutical preparation 1).

Furthermore, the above-mentioned mixture (80 g) of hydrogenated castor oil and talc was spread to the core in the same way as mentioned above, thereby the mixture adhering to the core. A sustained release pharmaceutical preparation wherein the ratio of the amount of the coating layer was 40% to that of the core was thus obtained (Pharmaceutical preparation 2).

EXAMPLE 2

The procedure was carried out in the same manner as in Example 1 except for using a mixture (40 g, 60 g or 80 g) of hydrogenated castor oil having the mean particle diameter of 25 μm and magnesium stearate having the mean particle diameter of 15 μm in the ratio of 2:8 instead of the mixture of hydrogenated castor oil and talc. Sustained release pharmaceutical preparations wherein the ratios of the amount of the coating layer were respectively 20%, 30% and 40% to that of the core were thus obtained (Pharmaceutical preparation 3, 4 and 5 respectively).

EXAMPLE 3

The procedure was carried out in the same manner as in Example 1 except for using a mixture (60 g or 80 g) of hydrogenated castor oil having the mean particle diameter of 25 μm and calcium stearate having the mean particle diameter of 5 μm in the ratio of 2:8 instead of the mixture of hydrogenated castor oil and talc. Sustained release pharmaceutical preparations wherein the ratios of the amount of the coating layer were respectively 30% and 40% to that of the core were thus obtained (Pharmaceutical preparation 6 and 7 respectively).

EXAMPLE 4

Nonpareil having the diameter of 710 to 840 μm (250 g) was put into the centrifugal fluidizing type granulating and coating apparatus (CF-360) and rolled in it at 90° C. With rolling the Nonpareil, thereto was gradually spread a mixture of nicotiamide having the diameter of 5 to 50 μm (176 g), talc having the mean particle diameter of 10 μm (20 g) and hydrogenated castor oil having the mean particle diameter of 25 μm (44 g), thereby the mixture adhering to the Nonpareil. Thus a core was prepared. No dusting of powder nor agglomeration of carrier and/or core was observed during the preparation of the core. Successively, with rolling the core (200 g) in the above-mentioned apparatus at 90° C., thereto was gradually spread each mixture (30 g) of polyethyleneglycol 6000 having the mean particle diameter of 100 μm, hydrogenated caster oil having the mean particle diameter of 25 μm and magnesium stearate having the mean particle diameter of 20 μm in the ratio of 0:2:8, 5:15:80, 1:1:8 or 2:0:8, thereby the mixture adhering to the core. Thus four kinds of sustained release pharmaceutical preparations wherein the ratio of the amount of the coating layer was 15% to that of the core were obtained.

EXAMPLE 5

The procedure was carried out in the same manner as in Example 4 except for using a mixture (75 g) of hydrogenated rape seed oil having the mean particle diameter of 30 μm and ethylcellulose having the mean particle diameter of 5 μm in the ratio of 35:65 instead of the mixture of polyethylene glycol 6000, hydrogenated castor oil and magnesium stearate. A sustained release pharmaceutical preparation wherein the ratio of the amount of the coating layer was 15% to that of the core was thus obtained.

EXAMPLE 6

With rolling the core (500 g) obtained in the same way as in Example 4 at 70° C., thereto was spread a mixture (150 g) of stearyl alcohol having the diameter of at most 250 μm and titanium dioxide having the mean particle diameter of 0.4 μm in the ratio of 1:9, thereby the mixture adhering to the core. A sustained release pharmaceutical preparation wherein the ratio of the amount of the coating layer was 30% to that of the core was thus obtained.

EXAMPLE 7

With rolling the core (500 g) obtained in the same way as in Example 4 at 80° C., thereto was spread a mixture (150 g) of stearic acid having the diameter of at most 250 μm, talc having the mean particle diameter of 10 μm and precipitated calcium carbonate having the mean particle diameter of 10 μm in the ratio of 2:6:2, thereby the mixture adhering to the core. A sustained release pharmaceutical preparation wherein the ratio of the amount of the coating layer was 30% to that of the core was thus obtained.

EXAMPLE 8

Nonpareil having the diameter of 710 to 840 μm (250 g) was put into the centrifugal fluidizing type granulating and coating apparatus (CF-360) and rolled in it at 90° C. With rolling the Nonpareil, thereto was gradually spread a mixture of theophylline having the diameter of 5 to 50 μm (189 g), talc having the mean particle diameter of 10 μm (21 g) and hydogenated castor oil having the mean particle diameter of 25 μm (40 g), thereby the mixture adhering to the Nonpareil. Thus a core was prepared. No dusting of powder nor agglomeration of carrier and/or core was observed during the preparation of the core. Successively with rolling the core (500 g) in the above-mentioned apparatus at 75° C., thereto was gradually spread each mixture (150 g) of hydrogenated rape seed oil having the mean particle diameter of 30 μm, talc having the mean particle diameter of 10 μm and lactose having the mean particle diameter of 50 μm in the ratio of 2:7:1 or 2:8:0, thereby the mixture adhering to the core. Thus two kinds of sustained release pharmaceutical preparations wherein the ratio of the amount of the coating layer was 30% to that of the core were obtained.

EXAMPLE 9

Purified sucrose having the diameter of 150 to 180 μm (1000 g) was put into the centrifugal fluidizing type granulating and coating apparatus (CF-360) and rolled in it at 75° C. With rolling the purified sucrose, thereto was gradually spread a mixture of diltiazem hydrochloride having the diameter of 5 to 50 μm (600 g), talc having the mean particle diameter of 10 μm (200 g) and hydogenated rape seed oil having the mean particle diameter of 30 μm (200 g), thereby the mixture adhering to the purified sucrose. Thus a core was prepared. No dusting of powder nor agglomeration of carrier and/or core was observed during the preparation of the core with rolling the core (1000 g) in the above-successively, mentioned apparatus at 75° C., thereto was gradually spread a mixture (1000 g) of hydrogenated rape seed oil having the mean particle diameter of 30 μm and talc having the mean particle diameter of 10 μm in the ratio of 2:8, thereby the mixture adhering to the core. Thus a sustained release pharmaceutical preparation wherein the ratio of the amount of the coating layer was 100% to that of the core was obtained.

EXAMPLE 10

Nonpareil having the diameter of 710 to 840 μm (500 g) was put into the centrifugal fluidizing type granulating and coating apparatus (CF-360) and rolled in it at 200 rpm at 35° C. With rolling the Nonpareil, thereto was gradually spread nicotiamide having the particle diameter of 5 to 50 μm (400 g) with spraying a 3% aqueous ethanol solution of 3% polyvinyl-pyrrolidone (300 g), thereby nicotinamide adhering to the Nonpareil. Thus a core was prepared. No dusting of powder nor agglomeration of carrier and/or core was observed during the preparation of the core. Successively, with rolling the core (500 g) in the above-mentioned apparatus at 90° C., thereto was gradually spread a mixture (150 g) of hydrogenated castor oil having the mean particle diameter of 25 μm and talc having the mean particle diameter of 10 μm in the ratio of 2:8, thereby the mixture adhering to the core. Thus a sustained release pharmaceutical preparation wherein the ratio of the amount of the coating layer was 30% to that of the core was obtained.

TEST EXAMPLE 1

The dissolution test according to the puddle method (37° C., 900 mλ of water, 100 rpm) based on the specification of the dissolution test under 11th revised Japanese Pharmacopocia (JPXI) was carried out with respect to each core and each sustained release pharmaceutical preparation (Pharmaceutical preparation 1 to 7) obtained in Example 1, 2 or 3.

Figure 2:
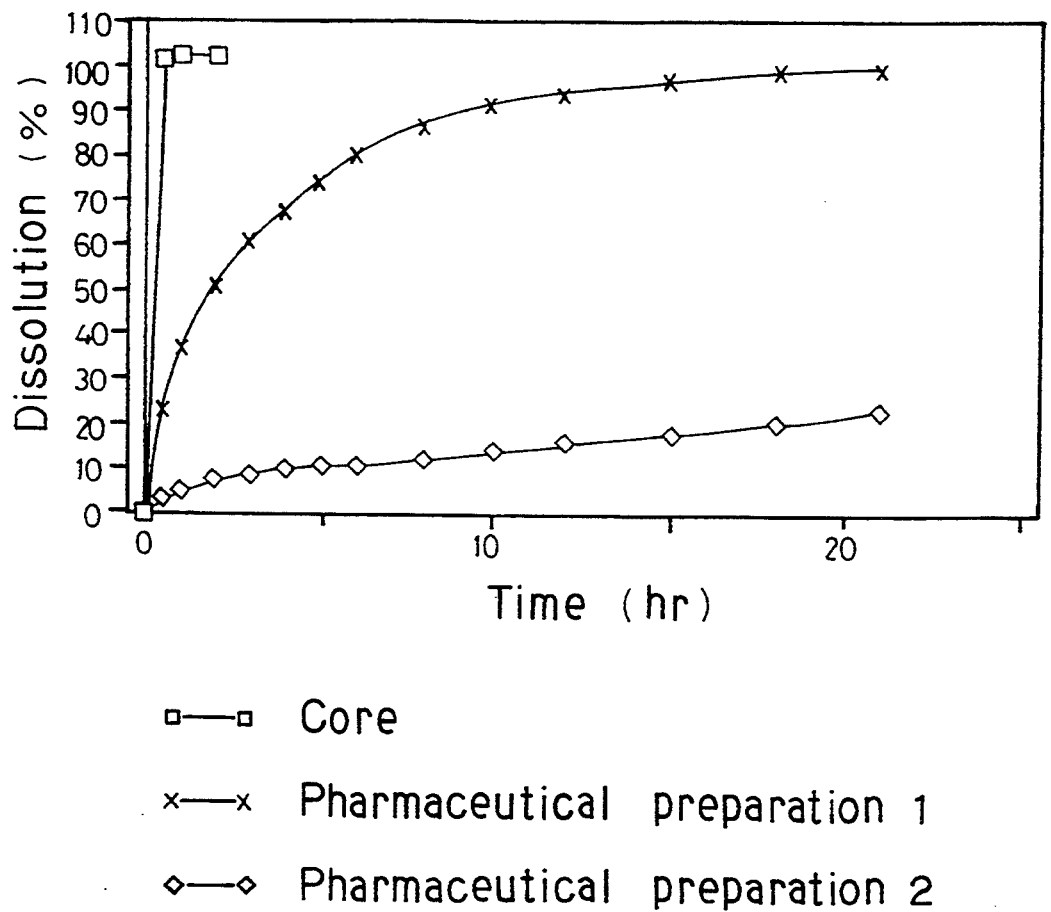
FIG. 2 is a graph showing the result of the dissolution test in Test Example 1 as to sustained release pharmaceutical preparations obtained in Example 1.
Figure 3:
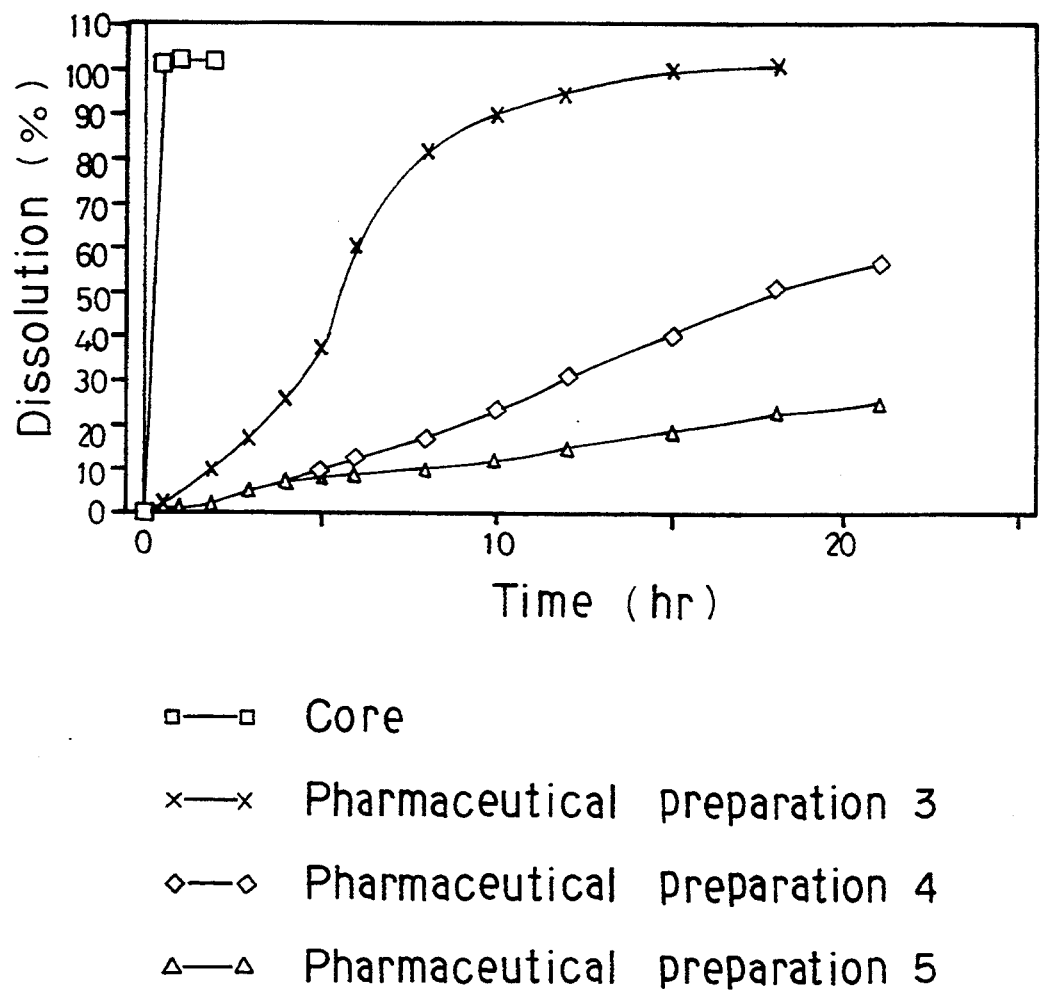
FIG. 3 is a graph showing the result of the dissolution that in Test Example 1 as to sustained release pharmaceutical preparations obtained in Example 2.
Figure 4:
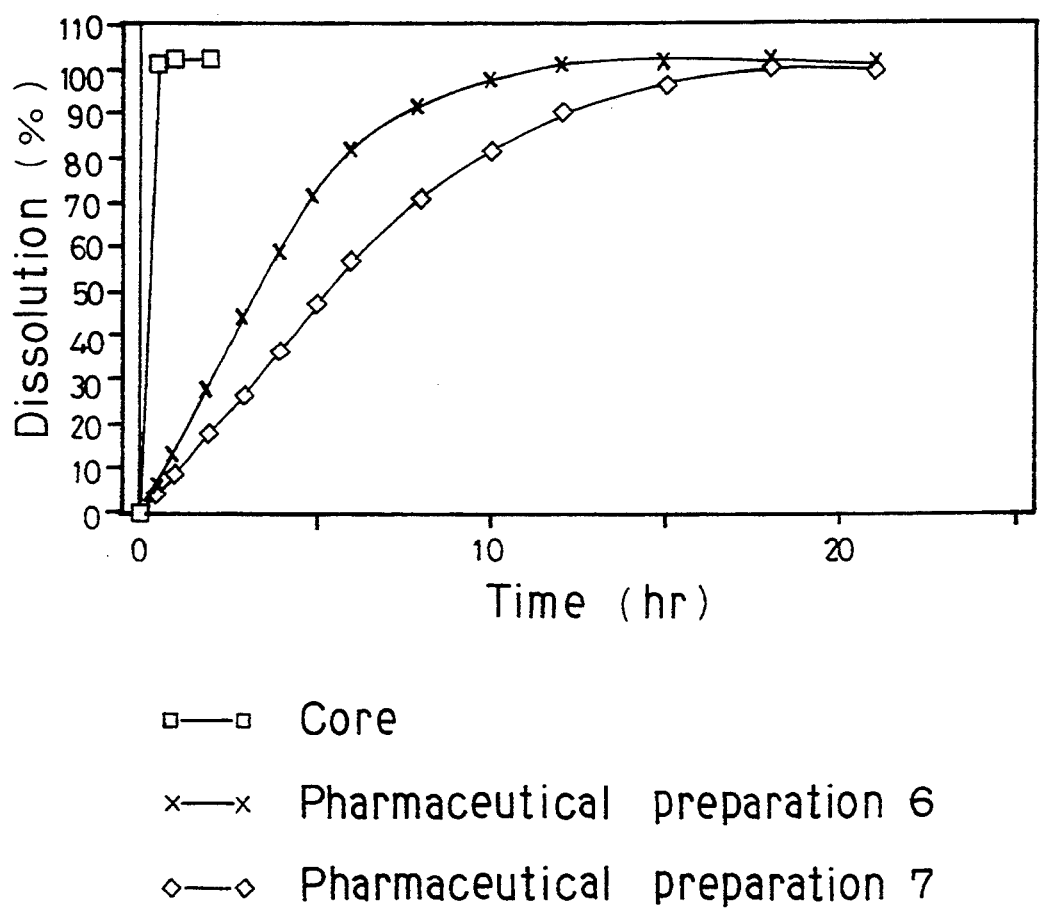
FIG. 4 is a graph showing the result of the dissolution test in Test Example 1 as to sustained release pharmaceutical preparations obtained in Example 3.

The results of the dissolution tests are shown in FIGS. 2 to 4. As shown in Figures, it is recognized that the dissolution rate is controlled in every sustained release pharmaceutical preparation of the present invention and that the dissolution rate can be controlled by selecting the coating amount (percentage).

What is claimed is:

1. A process for preparing a sustained release pharmaceutical preparation which comprises:
    (1) adding a mixture containing a medicinal compound and a heat-meltable material to a particulate carrier while tumbling the carrier at a temperature at which the heat-meltable material can melt, to form an effective ingredient layer containing the medicinal compound and the heat-meltable material as a binder around the carrier, thereby providing a core, and
    (2) successively adding a mixture containing a heat-meltable material and a non-heat-meltable dissolution-controlling agent to the core under the same condition as in the step (1) to form a coating layer containing the non-heat-meltable dissolution-controlling agent and the heat-meltable material as a binder around the core;
    wherein the heat-meltable material is selected from the group consisting of a saturated or unsaturated fatty acid having 10–32 carbon atoms, an aliphatic monatomic alcohol having 12–30 carbon atoms, an ester of a saturated or unsaturated fatty acid having 14–24 carbon atoms and an aliphatic monaromic alcohol having 12–24 carbon atoms, an ester of a saturated or unsaturated fatty acid having 12–18 carbon atoms and glycerin, an ester of a hydroxyl group-containing fatty acid having 12–22 carbon atoms and an aliphatic monatomic alcohol having 12–22 carbon atoms, an ester of a hydroxy group-containing saturated fatty acid having 12–22 carbon atoms and glycerin, an ester of a hydroxy group-containing unsaturated fatty acid having 12–22 carbon atoms and glycerin, a hydrogenated compound of any of said esters and a polyethyleneglycol;
    wherein the non-heat-meltable dissolution-controlling agent is selected from the group consisting of magnesium stearate, calcium stearate, talc, titanium dioxide, colloidal silicon dioxide, magnesium silicate, dried aluminum hydroxide gel, precipitated calcium carbonate and calcium sulfate; and
    with the proviso that the effective ingredient layer and the coating layer are formed without using solvents.

2. The process of claim 1, wherein the heat-meltable material is selected from the group consisting of an ester of a saturated or unsaturated fatty acid having 14–24 carbon atoms and an aliphatic monatomic alcohol having 12–24 carbon atoms, an ester of a saturated or unsaturated fatty acid having 12–18 carbon atoms and glyceline and a hydrogenated compound thereof.

3. The process of claim 1, wherein the heat-meltable material is selected from the group consisting of hydrogenated castor oil, a polyethyleneglycol, hydrogenated rape seed oil, stearyl alcohol and stearic acid.

4. The process of claim 1, wherein the non-heat-meltable dissolution-controlling agent is selected from the group consisting of magnesium stearate, calcium stearate, talc, titanium dioxide and precipitated calcium carbonate.

5. The process of claim 3, wherein the non-heat-meltable dissolution-controlling agent is selected from the group consisting of magnesium stearate, calcium stearate, talc, titanium dioxide and precipitated calcium carbonate.

* * * * *